(12) United States Patent
Patel

(10) Patent No.: US 10,610,507 B2
(45) Date of Patent: Apr. 7, 2020

(54) METHODS FOR THE TREATMENT OF SIALORRHEA

(71) Applicant: NeuRX Pharmaceuticals LLC, Salt Lake City, UT (US)

(72) Inventor: Dinesh C. Patel, Salt Lake City, UT (US)

(73) Assignee: NeuRx Pharmaceuticals LLC, Salt Lake City, UT (US)

( * ) Notice: Subject to any disclaimer, the term of this patent is extended or adjusted under 35 U.S.C. 154(b) by 0 days.

(21) Appl. No.: 16/133,072

(22) Filed: Sep. 17, 2018

(65) Prior Publication Data

US 2019/0015371 A1   Jan. 17, 2019

Related U.S. Application Data

(60) Continuation of application No. 15/628,456, filed on Jun. 20, 2017, which is a division of application No. 14/539,734, filed on Nov. 12, 2014, now abandoned, which is a continuation-in-part of application No. 13/675,778, filed on Nov. 13, 2012, now abandoned.

(51) Int. Cl.
| | |
|---|---|
| *A61K 31/216* | (2006.01) |
| *A61K 9/20* | (2006.01) |
| *A61K 9/70* | (2006.01) |
| *A61K 9/00* | (2006.01) |

(52) U.S. Cl.
CPC .......... *A61K 31/216* (2013.01); *A61K 9/0056* (2013.01); *A61K 9/2009* (2013.01); *A61K 9/2018* (2013.01); *A61K 9/2054* (2013.01); *A61K 9/7061* (2013.01)

(58) Field of Classification Search
CPC .................................................. A61K 31/216
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,532,278 A | 7/1996 | Aberg et al. |
| 5,674,895 A | 10/1997 | Guittard et al. |
| 5,677,346 A | 10/1997 | Aberg et al. |
| 5,840,754 A | 11/1998 | Guittard et al. |
| 5,912,268 A | 6/1999 | Guittard et al. |
| 6,123,961 A | 9/2000 | Aberg |
| 6,262,115 B1 | 7/2001 | Guittard et al. |
| 2002/0002201 A1 | 1/2002 | Aberg |
| 2004/0057985 A1 | 3/2004 | Bracht |
| 2006/0078613 A1 | 4/2006 | Sanders et al. |
| 2008/0102102 A1 | 5/2008 | Merello et al. |
| 2011/0253133 A1 | 12/2011 | Martin et al. |

FOREIGN PATENT DOCUMENTS

| | | |
|---|---|---|
| WO | WO 92/20377 A1 | 11/1992 |
| WO | WO 01/93683 A1 | 12/2001 |

OTHER PUBLICATIONS

Leung et al.; "Immediate-Release Oxybutynin for the Treatment of Clozapine-Induced Sialorrhea"; The Annals of Pharmacotherapy; (Sep. 2011); e45, 5 pages; vol. 45.
Mayo Clinic; "Dry Mouth";(Apr. 7, 2011); 3 pages; http://www.mayoclinic.com/health/dry-mouth/HA00034; (accessed online Dec. 13, 2013).
Oki et al.; "In Vivo Demonstration of Muscarinic Receptor Binding Activity of N-desethyl-oxybutynin, Active Metabolite of Oxybutynin"; Life Sciences, Science Direct; (2005); pp. 2445-2456; vol. 76.

*Primary Examiner* — Yong S. Chong
(74) *Attorney, Agent, or Firm* — Arent Fox LLP

(57) ABSTRACT

The present invention provides safe and effective methods for the treatment of sialorrhea (excessive drooling) by administering an effective amount of N-desethyloxybutynin, or an optical R- or S-isomer thereof or a pharmaceutically acceptable salt thereof.

16 Claims, 1 Drawing Sheet

METHODS FOR THE TREATMENT OF SIALORRHEA

PRIORITY DATA

This application is a continuation of U.S. patent application Ser. No. 15/628,456, filed Jun. 20, 2017, which is a divisional of U.S. patent application Ser. No. 14/539,734, filed Nov. 12, 2014, which is a continuation-in-part of U.S. patent application Ser. No. 13/675,778 filed on Nov. 13, 2012, the content of each of which is incorporated herein by reference in its entirety.

FIELD OF INVENTION

The present invention relates to methods of treating sialorrhea (excessive drooling) by administering N-desethyloxybutynin to a subject in need of such treatment.

BACKGROUND OF THE INVENTION

Sialorrhea, commonly known as excessive drooling, or hypersalivation, is the inability to control oral secretions resulting in excessive accumulation and involuntary loss of saliva from the mouth. In a normal healthy individual, there is a balance between the production of saliva in the mouth by the salivary glands and the swallowing reflex which eliminates pooling of saliva from the oropharynx. When this balance is perturbed by increased saliva production and/or decreased swallowing reflex, it leads to the pooling of saliva in the mouth and consequent involuntary loss.

Sialorrhea is one of the major non-motor complaints in patients suffering from various neurological impairments, including Parkinson's disease, cerebral palsy, Amyotropic Lateral Sclerosis, Huntington's disease, stroke and traumatic brain injury. Sialorrhea is also a commonly occurring side effect of certain antipsychotic medications such as clozapine.

Sialorrhea leads to a range of physical and psychosocial complications including perioral chapping, dehydration, odor and social embarrassment and isolation. Sialorrhea is often described by these patients as one of the most significant disabling social problems of their disease. Depending on its severity, drooling can result in medical disability, impaired speech or serious eating difficulties.

Anticholinergic drugs, which are well known to produce "dry mouth" by reducing salivary flow have been used to treat patients suffering from sialorrhea. Recently the FDA approved a treatment of sialorrhea using glycopyrrolate in pediatric patients aged 3 to 16 years with neurologic conditions associated with problem drooling (e.g. cerebral palsy). It is available as 1 mg/5 ml oral solution. It has to be taken three times a day, one hour before or two hours after meals. The dose has to be carefully titrated for each patient from a low starting dose in increments of 0.02 mg/kg every 5-7 days.

SUMMARY OF THE INVENTION

The FDA approved treatment referenced above, as well as other off-label anticholinergic therapies have several undesirable anticholinergic side effects due to their activity at a variety of receptors and their propensity toward active metabolite formation. Consistent and accurate dosing is often difficult in view of the side effects that cause significant patient discomfort and inconvenience and which ultimately reduce therapeutic efficacy, tolerability, and patient compliance. Additionally, because of high degree of metabolism of most anticholinergics and inter-individual variation in metabolite formation, consistent standardized dosing across a population of individuals is also difficult if at all possible.

In view of the foregoing, the inventor has recognized a need for a drug treatment for sialorrhea that maximizes the therapeutic effect of reducing salivary flow, but minimizes side effects. Such therapy should be easy to administer with consistent absorption and consistent pharmacokinetics (including across a population of individuals) by having low susceptibility to metabolism, including first-pass metabolism, and high selectivity to the salivary glands (the target tissue for sialorrhea).

Accordingly, the present invention relates to a method of treating sialorrhea by administering a therapeutically effective amount of N-desethyloxybutynin, pharmaceutically acceptable salts of N-desthyloxybutynin, isomers of N-desethyloxybutynin, pharmaceutically acceptable salts of isomers of N-desethyloxybutynin or mixtures thereof to a subject in need of the treatment.

The methods of the present invention specifically encompass administration of N-desethyloxybutynin as a free base, a pharmaceutically acceptable salt, isomers of the free base or salt and the like. For example, the present invention also encompasses the administration of each isomer of N-desethyloxybutynin individually or in combination for the treatment of sialorrhea.

The N-desethyloxybutynin used in the present invention is administered as a suitable pharmaceutical dosage form or composition and may include pharmaceutically acceptable carriers and other ingredients as dictated by the particular needs of the dosage form. Such ingredients are well known to those skilled in the art. Previous references to N-desethyloxybutynin, merely recognize it as metabolite formed in situ following administration of oxybutynin. In stark contrast, the present invention is drawn to the direct administration of N-desethyloxybutynin (i.e. administration of this compound per se and not as a result of metabolizing another compound) for the treatment of sialorrhea, and the surprisingly superior results obtained therefrom as compared to oxybutynin. Generally, the prior art teaches that N-desethyloxybutynin is an undesirable result of oxybutynin administration and many references attempt to minimize or eliminate its formation.

Examples of suitable dosage forms for administration include oral, enteral, parenteral, buccal, transdermal, inhalant, implantable, vaginal or rectal type compositions. In one preferred aspect, the composition is an oral composition. In another aspect, the composition is an enteral composition, or the oral composition is enterally administered to a subject. In another aspect, the composition is a transdermal composition.

These and other embodiments of the invention, and their features and characteristics, will be described in further detail in the description and claims that follow.

DESCRIPTION OF EMBODIMENTS

For convenience, before further description of the present invention, certain terms employed in the specification, examples and appended claims are collected here. These definitions should be read in the light of the remainder of the disclosure and as understood by a person skilled in the art. Unless defined otherwise, all technical and scientific terms used herein have the same meaning as would be understood by a person of ordinary skill in the art.

The singular forms "a", "an" and "the" include plural references unless the context clearly dictates otherwise. Thus for example, reference to "an excipient" includes references to one or more of such excipients.

Figure 1:
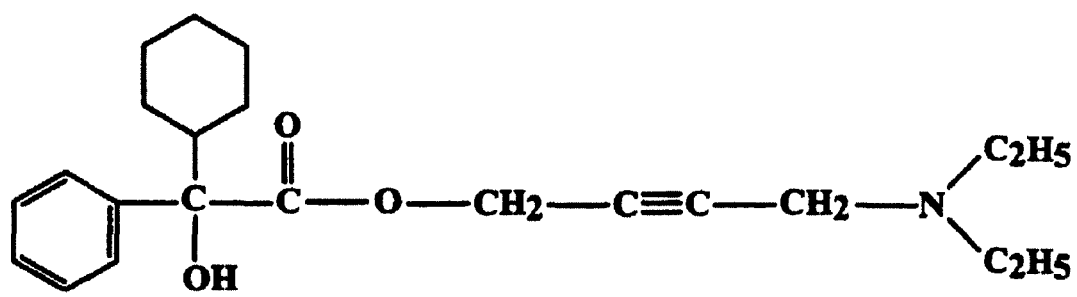
FIGS. 1 and 2 show a comparison of the chemical structures of oxybutynin and N-desethyloxybutynin.
Figure 2:
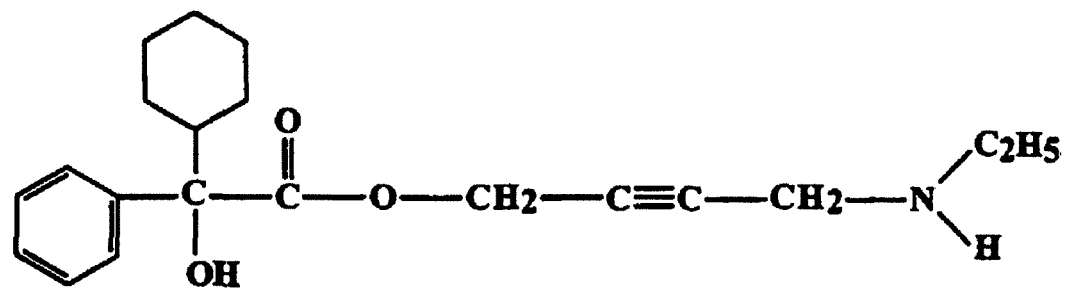

As used herein, "N-desethyloxybutynin" is a compound having the IUPAC name 4-(ethylamino) but-2-ynyl2-cyclohexyl-2-hydroxy-2-phenylacetate. N-desethyloxybutynin is also referenced in scientific literature as 4-ethylamino-2-butynyl cyclohexyl-phenylglycolate. Comparative structures of oxybutynin and N-desethyloxybutynin are shown in FIGS. 1 and 2. The recitation of "N-desethyloxybutynin" can include not only the free base compound, but also its R- and S-isomers and all functional salts thereof as well as isomers of the salts. However, such compounds may also be individually addressed when a higher level of specificity is desired, such as "N-desethyloxybutynin free base," or an "N-desethyloxybutynin salt," for example.

As used herein, the term "about" means that dimensions, formulations, parameters, and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

As used herein, "administration" and "administering" refers to the manner in which a drug is presented to a subject. "Direct administration" refers to administration of an agent that is responsible for a desired therapeutic effect in its unmetabolised form. Such direct administration may in some regards provide more potent and targeted therapies with a lower incidence of adverse or undesirable side effects as compared to indirect administration (i.e administration of an active agent for the purpose of receiving a therapeutic effect attributed primarily to an in-vivo metabolite thereof). Further, direct administration of an active agent is most often a more potent therapy than indirect administration. As such, a smaller amount of active agent can be delivered in order to achieve a therapeutic effect.

Administration can be accomplished by various routes well known in the art such as oral, enteral, parenteral, buccal, transdermal, inhalation, implantation, vaginal or rectal.

As used herein, "enteral" administration refers to administration through a subject's gastrointestinal tract.

As used herein, "parenteral" administration refers to a mode of administration that proceeds outside of a subject's digestive tract, but does not include transdermal or transmucosal administration. As such, "non-parenteral" administration encompasses any form of administration that proceeds through the digestive tract (i.e. enteral), and further includes administration through unbroken skin or through a mucosal membrane, such as that of the oral, nasal, rectal, or vaginal cavities.

As used herein, "oral administration" refers to administration that is either enteral, or transmucosal through the oral cavity, or a combination thereof. Thus, oral administration can be achieved by administering the drug as a solid e.g. pill, tablet (including buccal tablet), capsule, lozenge, adhesive, suppository and the like which may be retained in the oral cavity and dispense an active agent through the oral mucosa, or can be swallowed, chewed, or sucked. In some embodiments, oral administration can be enteral (i.e. when the formulation passes through the oral cavity (in either an altered or unaltered form) and into the downstream portions of the digestive tract. Oral administration can also be achieved by administering the drug as a liquid such as an oral solution, syrup or suspension of the drug. Oral administration includes immediate as well as controlled release formulations which encompass slow release, sustained release, extended release, prolonged release and delayed release. Parenteral administration can be achieved by injecting a drug composition intravenously, intra-arterially, intramuscularly, intrathecally or subcutaneously, etc. Parenteral administration includes immediate as well as controlled or sustained release formulations. Transdermal administration can be accomplished by applying, pasting, rolling, pouring, pressing, rubbing etc., of a transdermal composition onto a skin surface such as by means of a transdermal patch, creams, ointments etc. Transmucosal administration may be achieved by administering the drug to a subject through a mucosal membrane. As mentioned, one form of transmucosal administration is buccal administration through the oral mucosa. Buccal administration may in some aspects also be considered as a form of oral administration and can be achieved by means of compositions that are designed to dissolve in the mouth, adhere to the gum or inside of the cheek, or be held sublingually, etc. Transmucosal administration may also be achieved in some aspects by insertion of the drug into the nasal, vaginal, or anal cavities.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The term "pharmaceutically acceptable salts" used interchangeably with "salts", is recognized in the art and refers to salts prepared from relatively non-toxic acids or bases including inorganic acids and bases and organic acids and bases.

The terms "pharmaceutically acceptable carrier" and "carrier," as used herein are well known to those skilled in the art and may be used interchangeably and refers to any inert and pharmaceutically or nutritionally acceptable material with which the bioactive agent may be combined to achieve a specific dosage formulation for delivery to a subject. As a general principle, carriers do not react with the bioactive agent, or drug in a manner which substantially degrades or otherwise adversely affects the drug, or bioactive agent. Selection of carriers often depends on the type of dosage form. For a transdermal patch, the carrier can be a pressure sensitive adhesive into which the drug and other excipients are incorporated; the patch is then affixed to the skin to effect delivery of the drug. For a tablet dosage form, a powder carrier is formed by admixing the drug with excipients that can act as fillers, flow property modifiers, compressibility modifiers, control release agents, lubricants etc. that enable the powder to be compressed into a tablet. Other carriers conventionally known and used in the art are meant to be included in this definition unless specifically excluded.

As used herein, "excipient" and similar terms refers to substantially inert substances, which may be combined with an active agent and a carrier to achieve a specific dosage formulation for delivery to a subject, or to provide a dosage form with specific performance properties. For example, excipients may include binders, lubricants, etc., but specifically exclude active agents and carriers.

The term "subject" refers to a mammal that may benefit from the administration of N-desethyloxybutynin. Examples of subjects include humans as well as other warm-blooded animals such as horses, pigs, cattle, dogs, cats, rats or mice, etc. In one aspect the subject is a human.

The term "formulation" is used interchangeably with "composition".

The terms "drug", "active agent or ingredient," "bioactive agent," and "pharmaceutical" are also used interchangeably to refer to the pharmacologically active substance, i.e. N-desethyloxybutynin including isomers salts, mixtures as defined herein, present in the formulation or composition. These terms are well known in the pharmaceutical and medical arts.

As used herein, "effective amount" refers to an amount of N-desethyloxybutynin which, when included in a composition, is sufficient to achieve an intended compositional or physiological effect Thus, a "therapeutically effective amount" refers to a non-toxic, but sufficient amount of N-desethyloxybutynin, to achieve therapeutic results in treating or preventing a sialorrhea. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical and nutritional sciences as well as medicine. Effective amounts of a N-desethyloxybutynin may be administered in a single dose or multiple doses.

As used herein, "treat," "treatment," or "treating" refers to administration to subjects who are either asymptomatic or symptomatic. In other words, "treat," "treatment," or "treating" can be to reduce, ameliorate or eliminate symptoms associated with a condition present in a subject.

The term "mean", or "average" or similar terms when used in conjunction with the recitation of a number or numbers, means the sum of all the individual observations or items of a sample divided by the number of items in the sample.

If used, the phrase "area under the curve (AUC)" or "area under the plasma concentration-time curve" or similar terms are well known in the art.

DETAILED DESCRIPTION OF THE INVENTION

Sialorrhea, commonly known as excessive drooling, is defined as the inability to control oral secretions resulting in excessive accumulation and involuntary loss of saliva from the mouth. In a normal healthy individual, there is a balance between the production of saliva in the mouth and the swallowing reflex which eliminates the saliva from the oropharynx. When this balance is perturbed either by increased saliva production and/or decreased swallowing reflex, it leads to drooling, the pooling of saliva in the mouth and consequent involuntary loss.

Sialorrhea is one of the major non-motor complaints in patients suffering from various neurological impairments, including Parkinson's disease (PD), cerebral palsy, Amyotropic Lateral Sclerosis (ALS), Huntington's disease, stroke and traumatic brain injury. Sialorrhea is also a commonly occurring side effect of antipsychotic medications, particularly clozapine.

Sialorrhea may affect up to one million patients with diverse neurological diseases. It affects a large proportion of PD patients, ranging up to 78% in advanced stages, with many PD patients considering drooling as their worst non-motor symptom. Hypersalivation occurs in approximately one-third of schizophrenia patients treated with clozapine, a widely prescribed antipsychotic medication. Other large target populations include cerebral palsy patients and millions of survivors of stroke and severe traumatic brain injury.

Oxybutynin, an anticholinergic/antimuscarinic agent, is an approved drug for the treatment of urinary incontinence. Oxybutynin is available in oral as well as transdermal dosage forms and is marketed under such tradenames as Ditropan® (immediate release tablet), Ditropan® XL (extended release tablet), Oxytrol® (transdermal patch), and Gelnique® (transdermal gel).

Oxybutynin is a racemic mixture and has a chiral molecular center leading to the presence of (R)- and (S)-isomers. Particularly (R)-oxybutynin has been thought to be the more active of the two isomers, as indicated by animal pharmacological studies using isolated tissues.

N-desethyloxybutynin is a metabolite of oxybutynin and is present as a racemic mixture or isolated as the (R)- or (S)—N-desethyloxybutynin isomer. The structures of oxybutynin (OXY) and N-desethyloxybutynin (DEO) are shown in FIGS. 1 and 2.

When oxybutynin is administered orally it undergoes extensive first pass metabolism; the absolute bioavailability of oxybutynin is about 6%. Oxybutynin is metabolized primarily by the cytochrome P450 enzyme systems, particularly CYP3A4, found mostly in the liver and gut wall. Metabolites include phenylcyclohexylglycolic acid, which is pharmacologically inactive, and N-desethyloxybutynin, which is pharmacologically active. After oral administration of oxybutynin, pre-systemic metabolism results in an oral bioavailability of approximately 6.2% with large inter individual variation in oxybutynin plasma as evidenced by an 8-fold variation in maximal oxybutynin plasma concentration (Cmax) and a 13-fold variation in oxybutynin AUC. The variability in AUC is attributed mainly to variation in the rate of absorption and degree of first pass metabolism Therefore the blood levels of oxybutynin and consequently the N-desethyloxybutynin metabolite following oral administration of oxybutynin are highly variable. Additionally this variability in oxybutynin (and consequently N-desethyloxybutynin) pharmacokinetics can be compounded when other drugs that can induce or inhibit pre-systemic metabolism are co-administered with oxybutynin. For example, when oxybutynin is co-administered with ketoconazole, a potent inhibitor of Cytochrome P450 enzyme system, oxybutynin plasma levels increased by 3-4 fold compared to oxybutynin administration without ketoconazole.

As such relying on the metabolic production of N-desthyloxybutynin by pre-systemic metabolism following oral administration of oxybutynin as the primary means of generating N-desethyloxybutynin in blood for therapeutic effect will result in highly variable blood levels of N-desethyloxybutynin leading to highly inconsistent pharmacokinetics and pharmacological effects of N-desethyloxybutynin. Direct administration of N-desethyloxybutynin would be a much better option if it were more stable to first pass metabolism than oxybutynin, resulting in more consistent absorption, pharmacokinetics and pharmacological effects. N-desethyloxybutynin would thus represent a much better therapeutic option for the treatment of sialorrhea than administration of oxybutynin and reliance on indirectly generating N-desethyloxybutynin due to first pass metabolism to achieve therapy.

The inventors conducted human liver microsome incubation studies with oxybutynin and N-desethyloxybutynin to determine susceptibility of both compounds to first pass metabolism. The half-life and clearance values for oxybutynin and N-desethyloxybutynin are shown in Table 1 below.

TABLE 1

| Test Compound | Half Life (mins) | $Cl_{int}$ (ml/min/mg protein) |
|---|---|---|
| Oxybutynin | 5.2 | 0.267 |
| N-desethyloxybutynin | >60 (63.6) | 0.0218 |

This data clearly shows that N-desethyloxybutynin is at least an order of magnitude more stable to first pass metabolism than oxybutynin. This finding that N-desethyloxybutynin is 10 times more stable to metabolism by human liver microsomes than oxybutynin, is thought to be novel and unexpected.

This finding has very important implications for oral administration, including enteral administration of the two molecules. Direct oral administration of N-desethyloxybutynin will lead to more consistent absorption and less variable blood levels of N-desethyloxybutynin as compared to N-desethyloxybutynin blood levels generated as a consequence of first pass metabolism following direct oral administration of oxybutynin. Therefore the direct administration of N-desethyloxybutynin would represent a novel and unexpectedly better option for consistent pharmacokinetics of N-desethyloxybutynin and the treatment of sialorrhea as compared to reliance on the in-vivo generation of N-desethyloxybutynin by first-pass metabolism of orally administered oxybutynin. This important benefit of treating sialorrhea with direct administration of N-desethyloxybutynin instead of direct administration of oxybutynin followed by indirect generation of N-desethyloxybutynin following first-pass metabolism of oxybutynin is believed to have never before been realized or taught in the prior art. This benefit of direct administration of N-desethyloxybutynin for the treatment of sialorrhea becomes evident only from the metabolic stability data in Table 1.

Furthermore, because of the difference in susceptibility to first pass metabolism between oxybutynin and N-desethyloxybutynin, administration of N-desethyloxybutynin, including direct oral and/or enteral administration would have less drug-drug interaction potential than oxybutynin. This is another very important consideration in treating sialorrhea patients as there is a high likelihood that such patients will be receiving other medications for their primary neurological condition.

Moreover, N-desethyloxybutynin is more selective than oxybutynin for the parotid glands (glands behind or beside the ear, the salivary glands in humans and the target tissue for treatment of sialorrhea). Therefore it is safer than oxybutynin and other non-selective anticholinergics used alone or in combination with other agents for the treatment of sialorrhea. It is believed that there is no teaching or suggestion in the literature or prior art that N-desethyloxybutynin can be used to effectively treat sialorrhea and ameliorate the side effects commonly found when treating this excessive drooling condition.

Additionally, based on the chemical structures of oxybutynin and N-desethyloxybutynin (FIGS. 1 and 2 respectively), the logarithm of the octanol/water partition coefficient were calculated for the two compounds using ACD/ChemSketch Freeware (release 12.00; Product Version 12.01). The value for oxybutynin is 5.19 and that for N-desethyloxybutynin is 4.16. This strongly suggests that N-desethyloxybutynin is less lipophilic (less lipid soluble) than oxybutynin. Therefore N-desethyloxybutynin would be less likely to cross the blood brain barrier than oxybutynin. A direct consequence of this is that administration of N-desethyloxybutynin can be expected to have fewer central nervous system (CNS) effects than administration of oxybutynin. This is a very important consideration in the treatment of sialorrhea in patients with underlying neurological conditions such as Parkinson's disease, cerebral palsy etc., where CNS effects from the anticholinergic medication to control sialorrhea need to avoided as far as possible so as to not exacerbate the underlying neurological condition.

Moreover, the selectivity of N-desethyloxybutynin for the parotid glands (glands behind or beside the ear, the salivary glands in humans) also shows that it is potentially safer than other compositions, such as other anticholinergics used alone or in combination with other agents for the treatment of sialorrhea. It is believed that there is no teaching or suggestion in the literature or prior art that N-desethyloxybutynin can be used to effectively treat sialorrhea and ameliorate the side effects commonly found when treating this excessive drooling condition.

In summary, from a therapeutic standpoint, a sialorrhea patient would obtain more consistent pharmacokinetics and better efficacy from administration (including direct oral and/or enteral administration) of N-desethyloxybutynin than could be obtained by administering oxybutynin and attempting to rely on generation of N-desethyloxybutynin in the body as a consequence of first pass metabolism for a therapeutic effect. Furthermore, the metabolic stability and selectivity of N-desethyloxybutynin for the parotid glands make it the ideal anticholinergic for the treatment of sialorrhea in particular.

It has now been unexpectedly determined, based on the greater metabolic stability of N-desethyloxybutynin relative to oxybutynin, that N-desethyloxybutynin and its R- and S-isomers, when directly administered, can be more effective in the treatment of sialorrhea while having fewer side effects and better therapy than other anticholinergic agents that have been proposed or used in the treatment of this condition.

The overall process for preparing DEO involves: (a) the preparation of the side chain 4-ethylamino-2-butynyl chloride from dichlorobutyne (b) by standard esterification technique, reacting cyclohexylphenyl glycolic acid with 4-ethylamino-2-butynyl chloride to produce 4-ethylamino-2-butynyl cyclohexylphenyl-glycolate (DEO).

An alternative process for preparing DEO involves the preparation of a hydroxylated side chain instead of the above mentioned halogenated side chain.

A process for preparing R-DEO is described in U.S. Pat. No. 6,123,961 and a process for preparing S-DEO is described in U.S. Pat. No. 5,532,278, the disclosures of which are hereby incorporated by reference.

The magnitude of a prophylactic or therapeutic dose of the DEO compounds of this invention in the acute or chronic management of sialorrhea will vary with the severity and nature of the condition to be treated and the route of administration. The dose and the frequency of administration will also vary according to the age, body weight and response of the individual patient. In general, the total daily dose range for the compound of this invention for the conditions described herein is from about 1 mg to about 100 mg in single or divided doses, preferably in a single dose. In managing the subject, the therapy should be initiated at a lower dose, perhaps at about 5 mg to about 10 mg, and may be increased up to about 30-100 mg depending on the subject's global response. For immediate release dosages an oral dosage of about 1-30 mg administered once or multiple times a day could be adequate. For sustained release dosages an oral dosage of about 2-100 mg may be administered once or twice a day. It is further recommended that patients over 65 years and those with impaired renal or hepatic function initially receive low doses and that they be titrated based on individual response(s) and plasma drug level(s). It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat sialorrhea but insufficient to cause adverse effects" are encompassed by the above-described dosage amounts and dose frequency/schedule.

A wide range of suitable routes of administration may be employed for providing the subjectt with an effective dosage of the compounds of this invention. For example, oral, sublingual, rectal, parental (subcutaneous, intramuscular, intravenous), intraocular, transdermal, aerosol and like forms of administration may be employed. Dosage forms include tablets, controlled-release tablets, troches, dispersions, suspensions, solutions, syrups, capsules, microencapsulated systems, sprays, transdermal delivery systems, and the like.

The pharmaceutical compositions of the present invention comprise N-desethyloxybutynin, its isomers, salts and combinations thereof as defined above as the active ingredient, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Exemplary pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, succinic, sulfuric, tartaric, p-toluenesulfonic, and the like. The hydrochloride salt is particularly preferred for oral dosage forms.

The compositions of the present invention include suspensions, solutions, elixirs, powders or solid dosage forms (tablets and capsules). Carriers such as starches, sugars, and microcrystalline cellulose, diluents, granulating agents, lubricants, binders, disintegrating agents, and the like are suitable in the case of oral solid preparations (such as powders, capsules, and tablets). Oral solid preparations are preferred over the oral liquid preparations, except for administration in pediatric population where liquid dosage forms may be preferred.

Because of their ease of administration, tablets and capsules represent one of the more advantageous oral dosage unit forms, in which case solid pharmaceutical carriers are employed. If desired, tablets may be coated by standard aqueous or nonaqueous techniques. Since the compound of the invention has a relatively short duration of action in the body, it may be advantageous to administer the drug in a controlled-released or slow-release formulation, thereby decreasing the frequency of drug administration to the patient. The compounds of the present invention may also be administered by controlled release means and delivery devices such as those described in U.S. Pat. Nos. 3,845,770; 3,916,899; 3,536,809; 3,598,123; and 4,008,719, and PCT application WO92/20377, the disclosures of which are hereby incorporated by reference. Various forms of controlled release or slow release transdermal administration forms and devices known in the art can also be used to improve the convenience of dosage for the subject.

As previously noted, pharmaceutical compositions of the present invention suitable for oral administration may be presented as discrete unit dosage forms such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well known to persons of skill in the pharmaceutical art. Each tablet may contain from about 1 mg to about 100 mg of the active ingredient.

EXAMPLES

The following provides examples of N-desethyloxybutynin compositions in accordance with the present invention. They are meant to be exemplary only and do not restrict the invention.

Example 1—Stability of Oxybutynin and N-Desethyloxybutynin in Human Liver Microsome Incubation Study Human liver microsome incubation studies were conducted with oxybutynin and N-desethyloxybutynin to determine susceptibility of both compounds to first pass metabolism. The half-life and clearance values for oxybutynin and N-desethyloxybutynin are shown in Table 1 above. This data clearly shows that N-desethyloxybutynin is at least an order of magnitude more stable to first pass metabolism than oxybutynin.

Example 2—Preparation of an Immediate Release N-Desethyloxybutynin HCl Tablet

After being sieved through #60 mesh screen 10 g of N-desethyloxybutynin HCL is transferred into a clean container. To this is added 1 g of silicon dioxide powder and mixed thoroughly to form a uniform blend. Anhydrous lactose, 150 g, is sieved through a #60 mesh screen and transferred into a separate container. The N-desethyloxybutynin HCL-silicone blend and the lactose are then mixed thoroughly to obtain a uniform blend. To this uniform blend is added 1.5 g of magnesium stearate, which has also been sieved through a #60 mesh, which is then mixed thoroughly to again form a final uniform blend of active agent, silicon dioxide, lactose and magnesium stearate. Using a tablet press 162.5 mg portions of the final blend are pressed into tablets of the desired weight and shape each containing 10 mg of N-desethyloxybutynin HCl.

Example 3—Preparation of a Controlled Release N-Desethyloxybutynin HCl Tablet

After being sieved through a #60 mesh screen 30 g of N-desethyloxybutynin HCL is transferred into a clean container. To this is added 3 g of silicon dioxide powder and mixed thoroughly to form a uniform blend. Anhydrous lactose, 100 g, is sieved through a #60 mesh screen and transferred into a separate container. The active agent, silicon dioxide and anhydrous lactose are blended thoroughly and to this blend is added 450 g of Methocel K4M that has been sieved through a #60 mesh screen. This blend is mixed thoroughly and to this is added 5 g of Magnesium stearate which has also been sieved through a #60 mesh screen. This powder blend is mixed until a uniform powder blend is obtained.

Using a tablet press this blend of 588 g uniformly blended powder is pressed into tablets using appropriate tooling to from tablets of the desired weight and shape each tablet containing 30 mg of N-desethyloxybutynin in a controlled release form.

Example 4—Preparation of a Controlled Release N-Desethyloxybutynin HCl Tablet

After being sieved through a #60 mesh screen 15 g of N-desethyloxybutynin HCL is transferred into a clean container. To this is added 1.5 g of silicon dioxide powder and mixed thoroughly to form a uniform blend. Anhydrous lactose, 60 g, is sieved through a #60 mesh screen and transferred into a separate container. The active agent, silicon dioxide and anhydrous lactose are blended thoroughly and to this blend is added 150 g of Methocel K4M that has been sieved through a #60 mesh screen. This blend is mixed thoroughly and to this is added 1.5 g of Magnesium stearate which has also been sieved through a #60 mesh screen. This powder blend is mixed until a uniform powder blend is obtained.

Using a tablet press, this blend of 228 g of uniformly blended powder is pressed into tablets using appropriate tooling to from tablets of the desired weight and shape each tablet containing 15 mg of N-desethyloxybutynin in a controlled release form.

Example 5—Preparation of a Controlled Release N-Desethyloxybutynin Transdermal Patch The solids content of a pressure sensitive adhesive (PSA) (a solution of an acrylic adhesive polymer in organic solvents) is determined by weighing a small amount of adhesive solution in a pre-weighed aluminum dish. The solvent is then evaporated by overnight drying in a convection oven maintained at 70° C. and the percent solids adhesive content is determined from the ratio of the final dried weight to the initial solution weight.

To prepare a drug-containing adhesive film, 18 grams of the adhesive solution is weighed into a glass bottle. Assuming a percent solids adhesive content of 50%, this results in 9 grams of solid adhesive polymer. To this solution, 1 gram of N-desethyloxybutynin (free base) is added to yield a final desired dried film composition (% w/w) of acrylic adhesive/N-desethyloxybutynin 90/10. The glass bottle is tightly capped, sealed with parafilm, and rotated until the ingredients completely dissolve and the solution is visually clear.

Film casting of the adhesive-drug formulation is performed by dispensing approximately 10 ml of the adhesive/drug solution onto a polyester liner with a release coating and casting the solution as a thin film at a dry film coating weight of 6 mg/cm². The cast is dried in a convection oven at 70° C. for 15 minutes to yield the target dry film with a coating weight of 6 mg/cm². An occlusive polyethylene backing film is laminated onto the adhesive film to form a laminate. The laminate is then die-cut into 50 cm² patch and stored in sealed pouches. Each patch contains 30 mg of N-desethyloxybutynin.

Example 6—Administration of an Immediate Release N-Desethyloxybutynin HCl Tablet The tablet of Example 1 containing 10 mg of N-desethyloxybutynin is orally administered three times a day to a patient suffering from sialorrhea and results in a 33% reduction in drooling.

Example 7—Administration of a Controlled Release N-Desethyloxybutynin HCl Tablet The tablet of Example 2 containing 30 mg of N-desethyloxybutynin in controlled release form is orally administered once a day to a silaorrhea patient and results in 50% reduction in drooling within about 3 days of administration.

Example 8—Administration of a Controlled Release N-Desethyloxybutynin HCl Tablet The tablet of Example 3 containing 15 mg of N-desethyloxybutynin in controlled release form is orally administered twice a day to a silaorrhea patient and results in 50% reduction in drooling within about 3 days of initial dosing.

Example 9—Administration of a Controlled Release N-Desethyloxybutynin Transdermal Patch The transdermal patch of Example 4 is applied once daily to the upper arm of an individual suffering from sialorrhea resulting in 20% reduction in drooling within about 7 days of patch application.

The dosage form and the specific N-desethyloxybutynin form, i.e. salt, free base, R- and S-isomers or mixtures or isomers as specified above may be formulated and utilized in various dosages and forms, i.e. oral, buccal, transdermal, sublingual, injectable, and the like as would be obvious to one having ordinary skill in the art. It is to be understood that the above referenced compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements.

What is claimed is:

1. A method of treating sialorrhea comprising:
orally administering to a patient suffering from sialorrhea a therapeutically effective amount of N-desethyloxybutynin, or a pharmaceutically acceptable salt thereof.

2. The method of claim 1, wherein the N-desethyloxybutynin or a pharmaceutically acceptable salt thereof comprises (R)—N-desethyloxybutynin, (S)—N-desethyloxybutynin, pharmaceutically acceptable salts thereof, or a combination thereof.

3. The method of claim 1, wherein the N-desethyloxybutynin, or pharmaceutically acceptable salt thereof, is administered either transmucosally through the oral cavity or enterally, or by a combination thereof.

4. The method of claim 1, wherein the N-desethyloxybutynin or pharmaceutically acceptable salt thereof is administered as an immediate release dosage form.

5. The method of claim 1, wherein the N-desethyloxybutynin or pharmaceutically acceptable salt thereof is administered as a controlled release dosage form.

6. The method of claim 5, wherein the N-desethyloxybutynin or pharmaceutically acceptable salt thereof is administered as an extended release dosage form.

7. The method of claim 1, wherein the amount of N-desethyloxybutynin or pharmaceutically acceptable salt thereof is from about 1 mg to about 100 mg.

8. The method of claim 1, where in the amount N-desethyloxybutynin or pharmaceutically acceptable salt thereof is from about 2 mg to about 30 mg.

9. The method of claim 1, wherein the N-desethyloxybutynin or pharmaceutically acceptable salt thereof is administered as an oral tablet, capsule, liquid, or a powder.

10. The method of claim 1, wherein the N-desethyloxybutynin or pharmaceutically acceptable salt thereof is administered in a composition that dissolves in the mouth, adheres to the gum or inside of the cheek, or is held sublingually.

11. The method of claim 1, comprising orally administering a pharmaceutical composition comprising a therapeutically effective amount of N-desethyloxybutynin or a pharmaceutically acceptable salt thereof to the subject in need thereof.

12. The method of claim 1, wherein the patient is human.

13. The method of claim 12, wherein the human has a neurological condition.

14. The method of claim 13, wherein the neurological condition is Parkinson's disease, cerebral palsy, Amyotropic Lateral Sclerosis, Huntington's disease, stroke or traumatic brain injury.

15. The method of claim 13, wherein the human also receives medication for a neurological condition.

16. The method of claim 14, wherein the human also receives medication for a neurological condition.

* * * * *